United States Patent [19]

Harbolt et al.

[11] Patent Number: 4,610,714
[45] Date of Patent: Sep. 9, 1986

[54] APPARATUS AND METHOD FOR DISSOLVING UREA AND OTHER ENDOTHERMIC MATERIALS

[75] Inventors: Bruce Harbolt, Northride; Perry L. Murata, Torrance; Neal C. Burmaster, Anaheim, all of Calif.

[73] Assignee: Union Oil Company of California, Los Angeles, Calif.

[21] Appl. No.: 668,036

[22] Filed: Nov. 5, 1984

[51] Int. Cl.$^4$ .............................................. C05C 9/00
[52] U.S. Cl. ......................................... 71/28; 71/59; 71/61
[58] Field of Search .............. 264/14; 422/269; 71/28, 71/59, 61

[56] References Cited

U.S. PATENT DOCUMENTS 4,424,072 1/1984 Lerner ................................. 71/64.06
4,449,900 5/1984 Lerner ................................. 71/64.06

Primary Examiner—Ferris H. Lander
Attorney, Agent, or Firm—Dean Sandford; Gregory F. Wirzbicki; Robert J. Baran

[57] ABSTRACT

An energy efficient, economical method for dissolving urea, and other endothermic materials, e.g. potassium chloride, ammonium nitrate, etc., in water, without the use of fossil fuel-derived heat, which comprises: forming a slurry of such material and water, said slurry including said material as both a dissolved and solid phase; forming droplets of said slurry; and contacting said droplets of said slurry, in direct heat exchange relationship, with a moisture-containing air stream, having a temperature greater than the temperature of said droplets of said slurry, at conditions whereby both heat and moisture are removed from said moisture-containing air to thereby dissolve at least a portion of said solid phase. This process is especially useful for forming aqueous forming urea solutions, useful in agricultural applications and having from 19 to 23 percent, by weight, nitrogen. An apparatus, useful in said method, is also disclosed and claimed.

10 Claims, 1 Drawing Figure

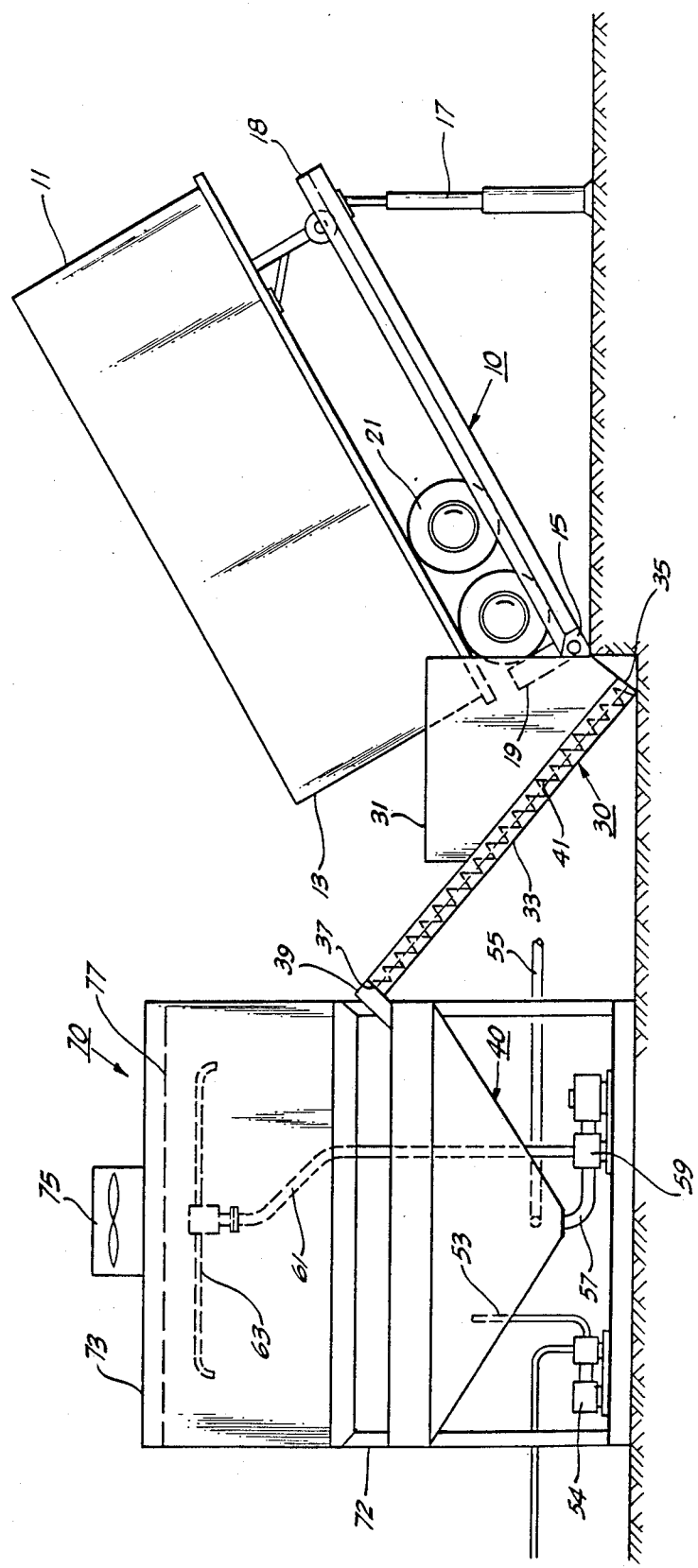

APPARATUS AND METHOD FOR DISSOLVING UREA AND OTHER ENDOTHERMIC MATERIALS

BACKGROUND OF THE INVENTION

1. Field of the Invention

This invention relates to an apparatus and method for dissolving endothermic materials, without the use of fossil-fuel derived heat. This invention is especially suitable for dissolving agricultural chemicals such as urea, potassium chloride, ammonium nitrate, etc.

2 Description of the Art

Commercial plants for dissolving endothermic materials such as urea and potassium chloride generally require fossil fuel-derived heat for efficient operation. This is due to the negative heat of solution for endothermic materials such as solid urea (The negative heat of solution for urea is approximately 109 BTUs per pound.) Thus, in the conventional fossil fuel-fired plant, hot water or steam and water at a temperature of approximately 180° F., are mixed with urea to produce a solution having a temperature of about 90° F. and 19 to 23 percent nitrogen. Unless adequate heat is supplied, this mixture becomes cold and rapidly approaches the crystallization temperature. Moreover the rate of dissolving is retarded and the production capacity is very low in the absence of sufficient heat.

It will be appreciated that it would be desirable to operate without fossil fuel-derived heat if such an operation could be economically carried out. Moreover, the elimination of fossil fuel from a process for dissolving endothermic material would be beneficial from the standpoint of conserving resources and, in addition, the pollution problems inherent in fossil fuel-derived heat would be avoided.

Thus it is one object of this invention to provide an energy efficient and economical method for dissolving endothermic materials without the use of fossil fuel-derived heat.

It is another object of the invention to provide a method and apparatus for dissolving endothermic materials which method and apparatus relies on natural environmental conditions, i.e. the weather.

It is another object of the invention to provide a process for dissolving endothermic materials which relies on the heat obtained from ambient air and thus it is particularly useful in locations wherein the average temperature of the ambient air is high, for example Hawaii.

Moreover, it is another object of this invention to take advantage of the temperature and humidity of the ambient air found in various locations to provide heat to a process for dissolving an endothermic material.

Finally, it is an object of the instant invention to provide a method and apparatus to prepare high concentrations of urea in water, for example 19 to 23 percent, by weight, nitrogen solutions, without the danger of crystallizing urea from such aqueous solutions and without the use of fossil fuel-derived heat.

Further objects and advantages are to provide improved steps, elements and arrangements thereof in a process effective in accomplishing the intended purposes.

Other objects and advantages of the instant invention will become apparent from a careful reading of the specification below.

SUMMARY OF THE INVENTION

This invention provides an energy efficient, economical method for dissolving urea, and other endothermic materials, e.g. potassium chloride, ammonium nitrate, sodium chlorate etc., in water, without the use of fossil fuel-derived heat, which comprises: forming a slurry of such material and water, said slurry including said material as both a dissolved and solid phase; and contacting said slurry, as droplets, in direct heat exchange relationship, with a moisture-containing air stream having a temperature greater than the temperature of said droplets of slurry, at conditions whereby both heat and moisture are removed from said moisture-containing air to thereby dissolve at least a portion of said solid phase. This method is especcially useful for forming aqueous urea solutions, useful in agricultural applications and having from 19 to 23 percent, by weight, nitrogen. In a method, for dissolving urea in water, in accordance with the present invention, a slurry comprising urea, as both the solid and dissolved phase, in an amount sufficient to yield a solution comprising from 19 to 23 percent, by weight, nitrogen, at a temperature of from about 36° to 64° F., is sprayed, as droplets, downwardly through an upwardly moving moisture-containing air stream, having a temperature of at least about 50° F. preferably from about 70° to 100° F. and a relative humidity of at least about 40 percent, preferably from about 70 to 100 percent, whereby heat and moisture are removed from said moisture-containing air. The sensible heat of the air and the heat derived by the condensation of moisture as well as the condensed moisture, itself, act to dissolve at least a portion of said solid urea phase.

BRIEF DESCRIPTION OF THE DRAWING FIGURE

The invention will be more readily understood by reference to the drawing FIGURE wherein a schematic diagram illustrating the process and apparatus of the instant invention is shown.

DETAILED DESCRIPTION OF THE INSTANT INVENTION

Referring now to the FIGURE of the drawing, a tilting platform shown generally at 10 is positioned contiguous to a screw conveyor-hopper unit 30 which feeds into mixing tank 40. Atop mixing tank 40 is positioned spray box 70.

In operation a truck trailer 11 is positioned on tilting platform 10 with its discharge end 13 adjacent to screw conveyor-hopper 30, as shown. Tilting platform 10 comprises a hinged end 15, adjacent screw conveyor-hopper 30. At the opposite end of tilting platform 10 a jack or hoist 17 is positioned and adapted to raise lifting end 18 of tilting platform 10. Tilting platform 10 also includes a block 19 against which the rear wheels 21 of trailer 11 are placed. Thus, when the platform is raised by action of jack 17, trailer 11 is tilted and the endothermic material contained therein may slide through open door (not shown) at the discharge end 13 of the trailer. Screw conveyor-hopper 30 includes a hopper 31 which is open at one side to enable the discharge end of trailer 11 to discharge into said hopper. A rising screw conveyor 33 is placed with one end 35 in the hopper and a second end 37 feeding into pipe 39 which discharges into mixing tank 40. Thus, endothermic material discharged into the hopper may be conveyed from within the hopper to discharge pipe 39 and ultimately into mixing tank 40. Screw conveyor 33 as shown is fitted with a rotatable screw element 41.

The endothermic material from the hopper is discharged into mixing tank 40 through discharge pipe 39. As shown, mixing tank 40 has upwardly slanted sides and a process water feed pipe 55 which passes through the slanted walls of mixing tank 40 and through which the process water may be fed by a pump (not shown). Mixing tank 40 also has a discharge pipe 57, providing an outlet at the bottom of mixing tank 40, for discharging the slurry of the endothermic material and water formed in mixing tank 40 therefrom. The mixing tank 40 is shaped so that the solid endothermic material tumbles down the slanted sides directly to the discharge pipe 57. Through this discharge pipe, by means of pump 59, is removed a slurry comprising a solution of said endothermic material and a solid phase comprising said endothermic material. As shown, the inlet of the process water feed pipe and the outlet of the slurry discharge pipe are in proximate relationship, whereby the incoming process water is substantially immediately removed from mixing tank 40 for turbulent mixing with the solid endothermic material. The rates of pumping the feed water and the slurry and the rate of feeding the solid endothermic material are regulated to ensure that the incoming process water and the solid endothermic material are substantially immediately removed from the mixing tank 40. The solid endothermic material and the incoming process water are slurried by pumping upward through pipe 61 to overhead spray pipe 63. During the passage through pipe 61 and overhead spray pipe 63 the above discussed turbulent mixing occurs.

In continuous operation, the solution containing the endothermic material, free of the solid phase, is removed through a solution discharge pipe 53 by means of pump 54. The outlet of solution discharge pipe 53 is preferably spaced laterally from and above the inlet of the process water feed pipe and the inlet of the slurry discharge pipe; thus, the solids-free solution may be continuously removed from the mixing tank without dilution by the incoming process water.

Overhead spray pipe 63 includes one or more orifices which can be oriented to either spray the slurry downwardly as droplets or upwardly and allow the droplets to free-fall back into mixing tank. Surrounding said overhead spray pipe 63 is spray box 70 which like mixing tank 40 is rectangular in cross section with the sides thereof registering with the sides of mixing tank 40. As shown, spray box 70 is supported by corner supports 72 which support both mixing tank 40 and spray box 70.

Spray box 70 is enclosed on all sides and the top, with only the bottom being open for the passage of the droplets back into the mixing tank. The bottom is fitted with a mesh or screen for supporting the packing within spray box 70. (The packing is not shown for easier illustration of the apparatus.) A fan opening (not shown) is provided in the roof 73 of spray box 70. The fan 75, positioned adjacent the fan opening, is operable to draw ambient air upwardly through the downwardly descending droplets of slurry. Within spray box 70 is also a demister 77 which is above overhead spray pipe 63 and prevents the escape of the slurry droplets through the fan opening. The demister may conveniently be a porous metal or plastic sheet.

In operation then, a truck may be used to position trailer 11 on tilting platform 10. By operation of the jack 17, the platform may be tilted to enable endothermic material contained in the truck to spill into hopper 31 for conveying by screw conveyor 33 into mixing tank 40. Water is continuously charged into mixing tank 40 through feed pipe 55 and is mixed with the solid endothermic material to form the desired slurry.

The slurry is continuously removed through discharge pipe 57 and by the turbulent mixing obtained as the slurry is pumped through pipe 61 to the overhead spray pipe, a major portion of the solid endothermic material is dissolved and the temperature of the slurry falls. (The slurry may comprise a saturated solution of the endothermic material or the solution may be unsaturated at the temperature obtained by the slurry in pipe 61 and/or overhead spray pipe 63.) The thus cooled slurry is sprayed as droplets downwardly from spray pipe 63 through an upwardly ascending ambient air stream drawn by fan 75. The droplets are of high surface area and thus efficiently heated by contacting, in direct heat exchange relationship, the upwardly ascending air stream. Moreover, moisture from such air stream condenses onto the droplets to provide further water and heat. The combination of heat and additional water, provided by condensing moisture vapor from the air, dissolves additional solid endothermic material in the droplets and thus as the droplets pass downwardly through the packing and fall into mixing tank 40 more endothermic material has been put into solution. The temperature of the downwardly descending droplets may remain the same or be slightly heated by the air stream since, by the mechanism of the method of the instant invention, the heat gained by condensing moisture vapor from the air and by heat exchange with the upwardly ascending air may be balanced by the heat required to dissolve additional solid phase. However, in efficient operation the air exiting the fan will be at a lower temperature than the air being drawn through spray box 70. In any event, this air will have a reduced moisture content as compared to the air being drawn into spray box 70 for heat exchange with the downwardly descending droplets. A concentrated solution of said endothermic material, free from solids, may be removed from solution discharge pipe 53, generally at a temperature at or near the crystallization temperature of the solution.

The method of the instant invention achieves maximum thermal efficiency by providing a zone of concentrated solids loading which permits continuous operation at or near the crystallization temperature of the liquid product produced. It is believed that this is accomplished by providing three process zones in the claimed apparatus:

Zone I—Solids Dissolution
Zone II—Solution Heating
Zone III—Solution Separation

In Zone I a relatively high-solids slurry comprising, as a minor portion, recycled slurry, and the slurry formed from the incoming process water and endothermic material, is vigorously mixed to rapidly lower the temperature thereof to below the crystallization temperature while dissolving a major portion of the solid endothermic material fed to the apparatus. Zone I comprises a small volume; however, the ability to provide this high rate of dissolution, in a small volume, is provided by the intense mixing and a high solids to liquid loading provided by pumping the high-solids slurry through pipe 61 and overhead spray pipe 63. The turbulence, that develops as the high-solids slurry is pumped directly through pipe 61 and the overhead spray pipe and is formed into droplets by passage through the orifice[s] of said spray pipe, provides a homogeneous slurry, without additional mechanical mixing, even though the temperature of the slurry is below the crystallization temperature. Moreover as the high-solids slurry passes through Zone I, the solid phase continuously dissolves, thereby lowering the temperature of the slurry and approaching or reaching the saturation point.

In Zone II, droplets of the concentrated slurry, having a temperature below the crystallization temperature, are subjected to direct air heating. As the temperature is raised to near or slightly above the crystallization temperature, for the given solution concentration, a major portion of, if not all of the solid endothermic material not dissolved in Zone I, is dissolved into the liquid phase.

In Zone III, a concentrated solution, at or near crystallization temperature, is removed from the mixing tank and the remaining solids settle to the bottom of the mixing tank and are returned to Zone I as the recycled slurry.

This process thus provides a means to operate at the lowest possible liquid temperatures, the widest possible air to solution temperature, and the highest possible production rate.

A preferred method of operating the process of the instant invention is as follows:

To obtain a solution, comprising 19 to 23 percent nitrogen and having a temperature above the crystallization point of urea, air at a temperature of at least 70° F. and a humidity of at least 70% may be contacted with the downwardly descending droplets of a slurry comprising urea as a solid and in solution. The amount of urea in the slurry is sufficient to provide, upon complete dissolution, a solution having the above concentration of dissolved nitrogen. The rate of flow of the air and the urea-containing slurry is adjusted so that the air exiting spray box 70 is at a temperature of less than about 50° F. and has a relative humidity of less than about 50%. The other process parameters are adjusted to ensure that the urea is substantially completely dissolved in one pass through the apparatus of the instant invention.

The invention is further illustrated by the following examples which are illustrative of a specific mode of practicing the invention and are not intended as limiting the scope of the appended claims.

EXAMPLE 1

Forty six thousand pounds of urea are discharged into mixing tank 40 at a rate of 920 pounds per minute. The feed water flow rate to mixing tank 40 is adjusted to 1193 pounds per minute (143 gallons per minute) at a temperature of 70° F. The product is withdrawn at a rate of 2,113 lbs/min. and at a temperature of 70° F. The upwardly ascending ambient air is pulled through spray box 70 at a flow rate of 53,187 cubic feet per minute, a temperature of 75° F., and a relative humidity of 70%. The slurry is recirculated through pipe 61 at the rate of approximately 7,600 pounds per minute. The amount of water and solid urea is chosen to provide a solution comprising 20% nitrogen. At steady state operation it is found that the temperature of the slurry as it passes through pipe 61 (Zone I) is 43° F.

EXAMPLE 2

In this example, potassium chloride is dissolved in water to provide a solution comprising 14.3% by weight potassium as $K_2O$. The same feed water temperature and ambient air is used in this example as in Example 1. The slurry recirculation rate through pipe 61 is also the same as in Example 1. The feed of potassium chloride is 920 pounds per minute into mixing tank 40 with a water flow rate of 2,944 pounds per minute (353 gallons per minute). Product is withdrawn at a rate of 3871 pounds per minute. The air flow rate is adjusted to provide an excess of heat to the downwardly descending droplets of potassium chloride slurry. In operation it is found that the temperature in Zone I is 50° F. Again, the dissolution of potassium chloride, like urea, is efficiently carried out without the use of fossil fuel-derived heat.

EXAMPLE 3

40,000 lb/hr of dry urea is fed into mixing tank 40 and a 45 percent by weight urea solution, at 50° F., is continuously withdrawn. The process feed water is at a temperature of 70° F. The relative humidity and the flow rate of air, at 75° F., is varied to determine the humidity and air flow rate requirements for efficient operation. The air rates and the moisture condensed from the air are tabulated below for air having a varying relative humidity.

| Percent Relative Humidity | Air, Dry Basis lb/hr | Wet Air $ft^3$/min | Water Condensing lb/hr |
|---|---|---|---|
| 2.2 | Infinite | Infinite | (Infinite Evaporation) |
| 5 | 3,328,000 | 748,400 | (−11,280 Evaporation) |
| 10 | 1,191,000 | 268,200 | (−2,950 Evaporation) |
| 25 | 406,000 | 91,830 | 114 |
| 50 | 194,000 | 44,190 | 956 |
| 100 | 93,400 | 21,600 | 1,356 |

The economic lower limit for operating the process of the instant invention would be between 10 percent and 25 percent relative humidity. That is, at 10 percent relative humidity and below, there is no condensation of moisture to provide heat to the slurry. Note that at a relative humidity of 50 percent, or more, the process of the instant invention is most efficient, i.e. the required airflow rate is reduced more than 50 percent, as the relative humidity increases from 25 to 50 percent, and more than another 50 percent as the relative humidity increases from 50 to 100 percent. For many conditions there is a minimum relative humidity below which the method of the instant invention is inefficient. (For the above conditions at below 2.2 percent relative humidity the invention is inoperable.) For practical purposes, the minimum relative humidity will be higher than this absolute theoretical minimum.

While particular embodiments of the invention have been described, it will be understood of course that the invention is not limited thereto since many obvious modifications can be made and it is intended to include within this invention any such modifications as will fall within the scope of the appended claims. For example, it will be appreciated by those skilled in the art in that the ambient air can be passed through spray box 70 in a cross direction as well as upwardly. Moreover, as discussed above, the droplets may be sprayed upwardly or downwardly and in either event they will free fall through the spraybox back to the mixing tank. Moreover, it will be understood that the apparatus described above can be operated on a continuous or a batch basis.

Having now described the invention, what it claimed is:

1. A method for dissolving an endothermic material in water which comprises the steps of,
   (a) forming a slurry of said endothermic material in water, said slurry comprising a solution of said endothermic material in water and an undissolved phase comprising said endothermic material,
   (b) forming droplets of said slurry of step (a),
   (c) contacting said droplets in direct heat exchange relationship, with a moisture-containing air stream having a temperature greater than said slurry, at conditions whereby both heat and moisture is removed from said moisture-containing air thereby dissolving at least a portion of said undissolved phase, and
   (d) recovering the product of step (c).

2. The method of claim 1 wherein said slurry is contacted, as downwardly descending droplets, with an upwardly moving, moisture-containing air stream.

3. The method of claim 2 wherein said upwardly moving air stream initially is at a temperature of at least about 50° F. and a relative humidity of at least about 40 percent.

4. The method of claim 3 wherein said slurry is at a temperature of less than about 64° F. prior to contacting with said upwardly moving air stream.

5. The method of claim 4 wherein said endothermic material is selected from the group consisting of urea, ammonium nitrate, potassium chloride sodium chlorate and mixtures thereof.

6. The method of claim 5 wherein said upwardly moving air stream has a relative humidity of greater than 90 percent.

7. The method of claim 6 wherein said endothermic material is urea.

8. The method of claim 7 wherein urea is admixed with ambient water to form a slurry at a temperature of from about 36° F. to about 64° F., and the product of step (c) is recovered as a solution comprising from about 19 to 23 percent, by weight, nitrogen, at a temperature above the crystallization point of urea and less than about 64° F.

9. A method for dissolving urea in water to provide a solution comprising from about 19 to 23 percent, by weight, nitrogen, which comprises:
   (a) admixing urea with ambient water to provide a slurry including a solid urea phase and a saturated solution of urea at a temperature of from about 36° to about 64° F.,
   (b) spraying said slurry of step (a) downwardly as droplets,
   (c) contacting said droplets, in direct heat exchange relationship, with an upwardly moving ambient, moisture-containing air stream having a temperature of at least 70° F. and a relative humidity of at least about 70 percent, to condense a portion of said moisture on said droplets and lower the temperature of said ambient air stream to less than 64° F., and
   (d) recovering said droplets and condensed moisture as a solution or urea comprising from 19 to 23 percent, by weight, and at a temperature above the crystallization point of urea.

10. A method for dissolving an endothermic material in water, without the use of fossil fuel-derived heat, which comprises:
   (a) spilling said endothermic material, as a solid, into a mixing zone comprising a mixing tank having slanted sides which join to define a slurry outlet;
   (b) passing a process water feed stream into said mixing zone at a point proximate said slurry outlet;
   (c) removing a high-solids slurry of said endothermic material and said process water through said slurry outlet, said slurry comprising a solution of said endothermic material in water and an undissolved phase comprising said endothermic material;
   (d) turbulently mixing said slurry to continuously dssolve a portion but not all of said undissolved phase and cool said slurry to a temperature below the crystallization temperature thereof, by pumping said slurry upwardly to a droplet forming zone comprising an overhead orificed spray pipe in fluid communication with said slurry outlet;
   (e) forming droplets of said cooled slurry by passing said cooled slurry through the orifices of said spray pipe;
   (f) allowing said droplets to fall into said mixing zone through an upwardly moving, moisture-containing air stream, having a temperature greater than said droplets, whereby both heat and moisture is removed from said moisture-containing air to thereby heat the droplets and dissolve at least an additional portion of said undissolved phase;
   (g) collecting said heated droplets in said mixing zone,
   (h) removing a solids-free solution comprising said endothermic material from a solution discharge pipe having an inlet spaced laterally from and above said slurry outlet; and
   (i) passing any remaining undissolved phase through said slurry outlet as a constituent of said high-solids slurry.

* * * * *